(12) United States Patent
Bransby et al.

(10) Patent No.: US 11,958,018 B2
(45) Date of Patent: *Apr. 16, 2024

(54) TANGENTIAL FLOW FILTRATION SYSTEMS AND METHODS

(71) Applicant: REPLIGEN CORPORATION, Waltham, MA (US)

(72) Inventors: Michael Bransby, Altadena, CA (US); Derek Carroll, Los Angeles, CA (US); Philip Yuen, Long Beach, CA (US); Ralf Kuriyel, Waltham, MA (US)

(73) Assignee: REPLIGEN CORPORATION, Waltham, MA (US)

( * ) Notice: Subject to any disclaimer, the term of this patent is extended or adjusted under 35 U.S.C. 154(b) by 703 days.

This patent is subject to a terminal disclaimer.

(21) Appl. No.: 17/091,616

(22) PCT Filed: May 28, 2019

(86) PCT No.: PCT/US2019/034152
§ 371 (c)(1),
(2) Date: Nov. 6, 2020

(87) PCT Pub. No.: WO2019/227095
PCT Pub. Date: Nov. 28, 2019

(65) Prior Publication Data
US 2022/0080359 A1     Mar. 17, 2022

Related U.S. Application Data

(60) Provisional application No. 62/676,411, filed on May 25, 2018.

(30) Foreign Application Priority Data

Mar. 8, 2019     (WO) ................ PCT/US2019/021414

(51) Int. Cl.
*B01D 61/14*     (2006.01)
*B01D 63/02*     (2006.01)
(Continued)

(52) U.S. Cl.
CPC ........... *B01D 63/06* (2013.01); *B01D 61/147* (2013.01); *B01D 63/02* (2013.01); *B01D 65/08* (2013.01);
(Continued)

(58) Field of Classification Search
CPC ................ B01D 63/06; B01D 2315/17; B01D 2321/20; B01D 2325/02; C12M 29/16
See application file for complete search history.

(56) References Cited

U.S. PATENT DOCUMENTS 3,095,343 A     6/1963     Berger
4,414,401 A    11/1983     Wintermeyer et al.
(Continued)

FOREIGN PATENT DOCUMENTS

CN    101578129 A    11/2009
CN    103619435 A     3/2014
(Continued)

OTHER PUBLICATIONS

Adema, E., and A. J. Sinskey. "An Analysis of Intra-Versus Extracapillary Growth In a Hallow Fiber Retractor." Biotechnology progress 3(2) (1987): 74-79.
(Continued)

*Primary Examiner* — Bradley R Spies
(74) *Attorney, Agent, or Firm* — KDW Firm PLLC

(57) ABSTRACT

The disclosure provides tangential flow depth filtration (TFDF) systems which exhibit improved filter fluxes and process capacities and reduced fouling characteristics. The TFDF systems of the disclosure optionally utilize tubular depth filters (TDF). Methods are provided which include the
(Continued)

passage of a non-laminar flow through at least a portion of a length of a TDF in a TFDF system.

19 Claims, 4 Drawing Sheets

(51) Int. Cl.
    *B01D 63/06*     (2006.01)
    *B01D 65/08*     (2006.01)
    *C12M 1/26*     (2006.01)

(52) U.S. Cl.
    CPC ......... *C12M 33/14* (2013.01); *B01D 2315/10* (2013.01); *B01D 2321/20* (2013.01)

(56) References Cited

U.S. PATENT DOCUMENTS

| | | | |
|---|---|---|---|
| 4,668,399 | A | 5/1987 | Duggins |
| 5,076,931 | A | 12/1991 | Muller |
| 5,607,766 | A | 3/1997 | Berger |
| 5,628,909 | A | 5/1997 | Bellhouse |
| 6,478,969 | B2 | 11/2002 | Brantley et al. |
| 6,544,424 | B1 | 4/2003 | Shevitz |
| 2005/0084536 | A1 | 4/2005 | Van Buitenen et al. |
| 2005/0197496 | A1 | 9/2005 | Perreault |
| 2006/0201876 | A1 | 9/2006 | Jordan |
| 2008/0131934 | A1 | 6/2008 | Crowley et al. |
| 2008/0217245 | A1 | 9/2008 | Rambod et al. |
| 2011/0210067 | A1 | 9/2011 | Kato et al. |
| 2011/0226689 | A1 | 9/2011 | Komori et al. |
| 2013/0153490 | A1 | 6/2013 | Pedersen et al. |
| 2014/0102982 | A1 | 4/2014 | Fairchild |
| 2014/0217013 | A1 | 8/2014 | Sato et al. |
| 2015/0125504 | A1 | 5/2015 | Ward et al. |
| 2016/0068565 | A1 | 3/2016 | Shibano et al. |
| 2016/0074569 | A1 | 3/2016 | Schuetz et al. |
| 2016/0199789 | A1 | 7/2016 | Ebara et al. |
| 2016/0222337 | A1 | 8/2016 | Serway |
| 2017/0292103 | A1 | 10/2017 | Cattaneo et al. |

FOREIGN PATENT DOCUMENTS

| | | |
|---|---|---|
| CN | 103998118 A | 8/2014 |
| CN | 104107589 A | 10/2014 |
| CN | 104548950 A | 4/2015 |
| DE | 19703877 C1 | 2/1998 |
| JP | H09117642 A | 5/1997 |
| JP | H10314553 A | 12/1998 |
| JP | 2006007224 A | 1/2006 |
| JP | 2009221137 A | 10/2009 |
| JP | 2013188711 A | 9/2013 |
| JP | 2017087097 A | 5/2017 |
| KR | 20050055039 A | 6/2005 |
| KR | 20090071549 A | 7/2009 |
| KR | 20170071476 A | 6/2017 |
| WO | 2008147785 A1 | 12/2008 |
| WO | 2011058983 A1 | 5/2011 |
| WO | 2012145787 A1 | 11/2012 |
| WO | 2017180573 A1 | 10/2017 |
| WO | 2019173752 A1 | 9/2019 |

OTHER PUBLICATIONS

International Search Report and Written Opinion dated Aug. 2, 2019 for International Application, PCT/US2019/021414 filed Mar. 8, 2019.
Gailliot F P: Methods in Biotechnology, Humana Press. vol. 4, 1998, pp. 53-89.
European Search Report for the European Application No. 19807976, dated Jun. 14, 2022, 15 pages.
Extended European Search Report dated Apr. 2, 2021 for corresponding European Patent Application No. 19764619.3, dated Jan. 4, 2021, 8 pages.
Gailliot F P: "Initial Extraction and Product Capture", Methods in Biotechnology, Humana Press, vol. 4, Jan. 1, 1998.
European Search Report and Written Opinion for Application No. EP19807976, dated Mar. 25, 2022, 16 pages.
The Engineering Toolbox, "Laminar, Transition or Turbulent Flow," Datasheet [online]. Oct. 23, 2017, retrieved from Internet: <https://web.archive.org/web/20171023112205/http://www.engineeringtoolbox.com/laminar-transitional-turbulent-flow-d_577.html>, p. 1, para 5.
Shin-ichi Nakao, "Membrane Engineering—What we know and What we don't know," Membrane, vol. 36, Issue 5, 2011, pp. 204-210.

TANGENTIAL FLOW FILTRATION SYSTEMS AND METHODS

CROSS-REFERENCE TO RELATED APPLICATIONS

This application claims the benefit of priority under 35 USC § 119 to U.S. Provisional Patent Application Ser. No. 62/676,411, filed May 25, 2018, and to PCT application No. PCT/US2019/021414 filed Mar. 8, 2019, both of which are incorporated by reference herein in their entirety and for all purposes.

FIELD OF THE DISCLOSURE

The present disclosure relates to systems and methods for filtration, particularly to tangential flow depth filtration (TFDF).

BACKGROUND

Filtration is typically performed to separate, clarify, modify and/or concentrate a fluid solution, mixture or suspension. In the biotechnology and pharmaceutical industries, filtration is vital for the successful production, processing, and testing of new drugs, diagnostics and other biological products. For example, in the process of manufacturing biologicals, using animal or microbial cell culture, filtration is done for clarification, selective removal and concentration of certain constituents from the culture media or to modify the media prior to further processing. Filtration may also be used to enhance productivity by maintaining a culture in perfusion at high cell concentration.

Tangential flow filtration (also referred to as cross-flow filtration or TFF) systems are widely used in the separation of particulates suspended in a liquid phase, and have important bioprocessing applications. In contrast to dead-end filtration systems in which a single fluid feed is passed through a filter, tangential flow systems are characterized by fluid feeds that flow across a surface of the filter, resulting in the separation of the feed into two components: a permeate component which has passed through the filter and a retentate component which has not. Compared to dead-end systems, TFF systems are less prone to fouling. Fouling of TFF systems may be reduced further by alternating the direction of the fluid feed across the filtration element as is done in the XCell™ alternating tangential flow (ATF) technology commercialized by Repligen Corporation (Waltham, Mass.), by backwashing the permeate through the filter, and/or by periodic washing.

Modern TFF systems frequently utilize filters comprising one or more tubular filtration elements, such as hollow-fibers or tubular membranes. Where tubular filtration elements are used, they are typically packed together within a larger fluid vessel, and are placed in fluid communication with a feed at one end and at the other end with a vessel or fluid path for the retentate; the permeate flows through pores in the walls of the fibers into the spaces between the fibers and within the larger fluid vessel. Tubular filtration elements provide large and uniform surface areas relative to the feed volumes they can accommodate, and TFF systems utilizing these elements may be scaled easily from development to commercial scale. Despite their advantages, TFF systems filters may foul when filter flux limits are exceeded, and TFF systems have finite process capacities. Efforts to increase process capacities for TFF systems are complicated by the relationship between filter flux and fouling.

SUMMARY OF THE DISCLOSURE

The present disclosure provides TFF systems with improved process capacities by reducing fouling characteristics while increasing filter flux. In its various aspects, the disclosure provides systems and methods for TFF which employ non-laminar feed flows through tubular depth filters (TDFs). These systems are referred to throughout this specification as tangential flow depth filtration systems or TFDF systems.

In one aspect, the present disclosure relates to a tangential flow depth filtration (TFDF) system that includes a filter having first and second ends and comprising at least one tubular depth filter unit (TDF) extending between and open to each of the first and second ends of the filter, a first vessel in fluid communication with the first end of the filter and the at least one TDF and a pump configured to drive a fluid flow through the first vessel and the filter such that a Reynolds number (Re) at the first end of the filter is greater than 2000, 2300, 2500, 3000, 3500 or 4000. The system utilizes TDFs having an inner diameter of at least 1 mm and comprising a porous wall having a thickness of at least 100 μm, though in certain embodiments each TDF has an inner diameter of 2 mm. In some embodiments, the pump is configured to provide a feed velocity greater than 2 m/s. Some embodiments of the system include a second vessel fluidly isolated from the first and second ends of the filter and in fluid communication with at least one external surface of the at least one TDF and/or a third vessel fluidly connected to the second end of the filter and the at least one TDF. In these embodiments, operation of the pump may drive vessel through the at least one TDF and into the second and third vessels, and in some of these embodiments, a flow of fluid through the at least one TDF between the first and third vessels is non-laminar.

Another aspect of this disclosure relates to a TFDF system that includes a filter with at least one TDF, which system is configured to drive a non-laminar flow through at least a portion of the filter. In various embodiments, the system is configured to operate at shear rates below 16,000 s$^{-1}$.

Various embodiments according to these aspects of the disclosure utilize TDFs comprising sintered or melt-blown polymers, which TDFs optionally have densities that are 50%, 51%, 52%, 53%, 54%, 55%, 56%, 57%, 58%, 59% or 60% of the density of an equivalent solid volume of the polymer. In some embodiments, the TDF has a pore size or first bubble point size between 0.2 and 5 microns, and/or an inner diameter between 0.75 and 13 mm, and/or a length between 200 and 2000 mm.

In another aspect, the disclosure relates to a method of filtering a fluid comprising passing the fluid through a TFDF system according to any of the foregoing aspects, such that the fluid flows in a non-laminar manner through the at least one TDF. In various embodiments of the method, a product of a feed velocity of the system and an inner diameter of the at least one TDF is greater than 2500 mm$^2$s$^{-1}$ and/or is 2000, 2300, 2500, 3000, 3500 or 4000 times greater than the quotient of a kinematic viscosity of the fluid over the TDF diameter d. The direction of flow through the filter is alternated in some cases. In various embodiments of the method, the filter may retain a non-desired species, which may be selected from the group consisting of: a species of mammalian cell origin; a species of microbial cell origin; a species of viral origin; a protein; a nucleic acid; a polysaccharide; or a complex of any of the foregoing. The method may also involve collection of a filter permeate. In some embodiments, the filter permeate comprises a desired species (e.g., a species of mammalian cell origin; a species of microbial cell origin; a species of viral origin; a protein; a nucleic acid; a polysaccharide; a virus; a microcarrier; a particle; or a complex of any of the foregoing), while in other embodiments the desired species is retained by the filter and is concentrated over time by removal of the filtrate without replacement of the lost volume.

In another aspect, the disclosure relates to a composition comprising a filter permeate generated by a method according to the foregoing aspect of the disclosure. A concentration of a desired species in the composition can be at least 10×, 20×, 40×, 50×, 75× or 100× greater than a concentration of the desired species in the fluid filtered in the method in some embodiments, and/or a concentration of a non-desired species is at least 10×, 20×, 40×, 50×, 75× or 100× less than a concentration of the non-desired species in the fluid. In some embodiments, the desired species comprises a polypeptide, nucleic acid or polysaccharide.

The foregoing listing is intended to summarize, rather than limit, the following disclosure, and additional aspects or embodiments not set forth above may be appreciated by those of skill in the art.

DETAILED DESCRIPTION

Overview

The inventors have previously designed a tubular depth filter (TDF) for use in TFDF systems, as disclosed in commonly-owned PCT application no. PCT/US2019/021414, which application is incorporated by reference in its entirety and for all purposes. Specifically, the portions of PCT/US2019/021414 dealing with tubular depth filtration elements at ¶¶61-76, methods of making tubular depth filtration elements at ¶¶77-88, and applications of TFDF systems utilizing tubular depth filtration elements at ¶¶89-103 are incorporated by reference.

Figure 1:
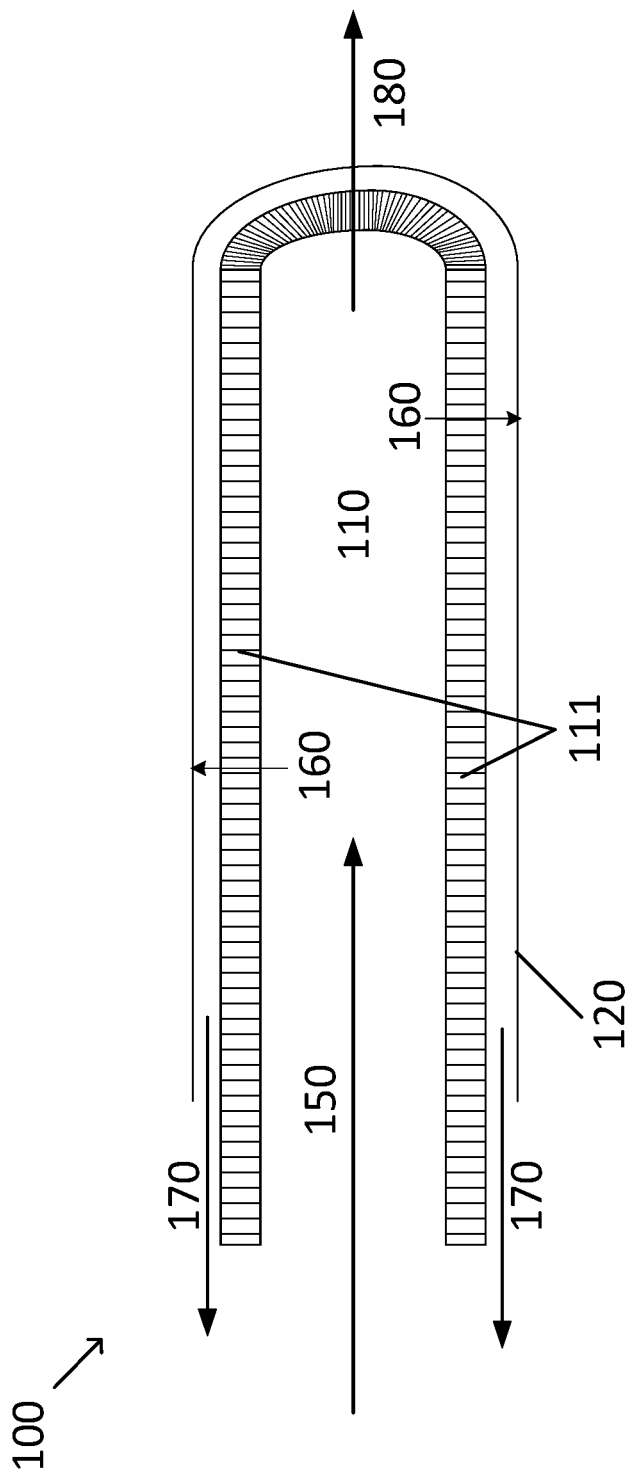
FIG. 1 is a cutaway diagram of a simplified (for illustrative purposes) TFDF system comprising a single tubular depth filtration element, depicting fluid feed, permeate and retentate flows.
Figure 2:
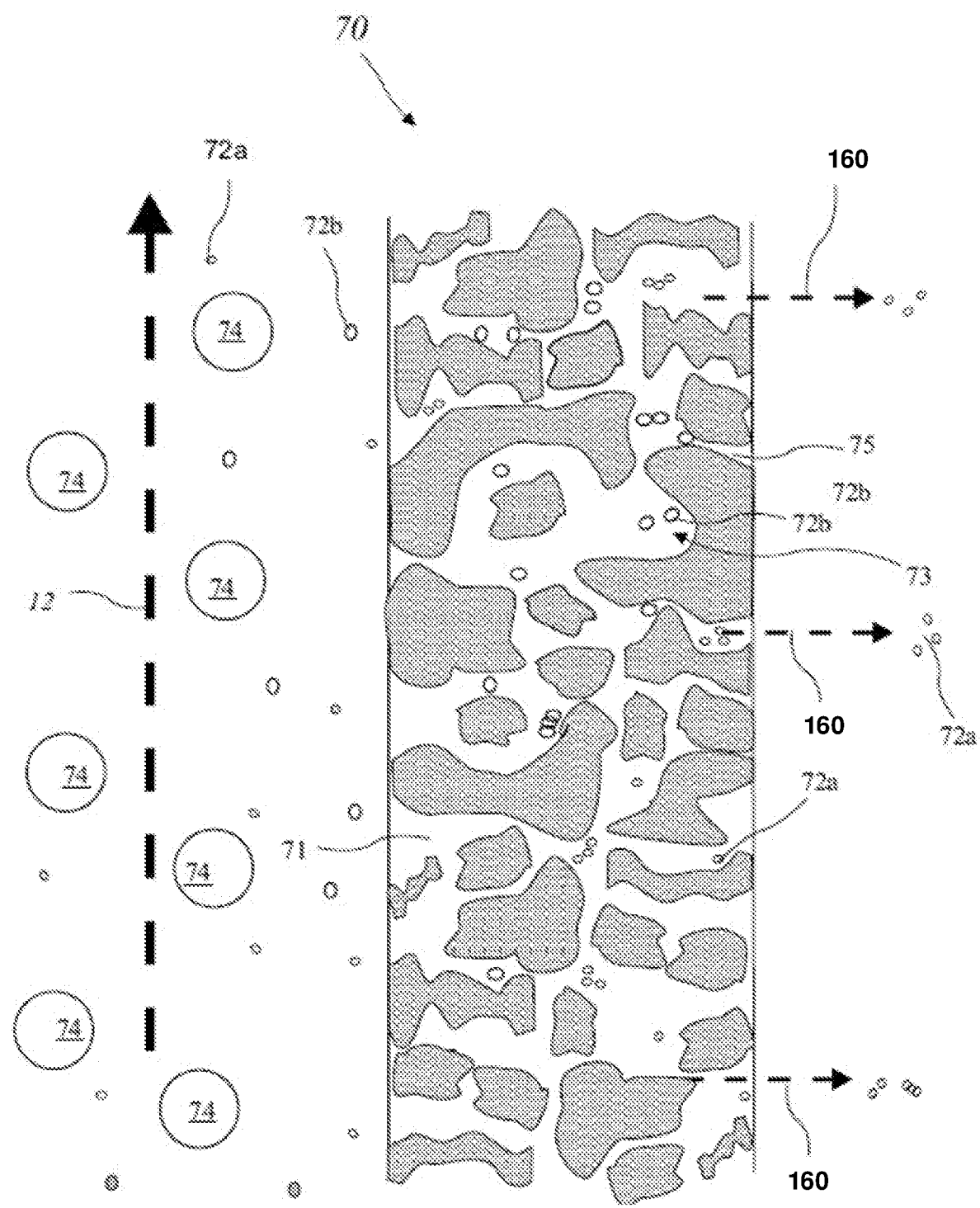
FIG. 2 is a cutaway depicting flows through the wall of a tubular depth filter according to certain embodiments of this disclosure.

FIGS. 1 and 2 depict an exemplary TFDF system 100, which includes a filter comprising at least one TDF 110 with a plurality of pores 111 in a wall thereof. The at least one TDF 110 is at least partially contained by a permeate vessel 120. In operation, a feed flow 150 enters the at least one TDF 110 and is separated into a plurality of flows 160 through the pores 111 of the TDF 110. The pore flows aggregate to form a permeate flow 170. The remainder of the feed flow 150 passes through the lumen of the TDF 110 as a retentate flow 180.

FIG. 2 depicts flows near a wall 70 of a single TDF 110 used in a TFDF system 100. In FIG. 2, a flow 12 along the wall 70 includes large particles 74, small particles 72a, and intermediate-sized particles 72b. The large particles 74 are generally larger than the average pore diameter on the inner surface of wall 70, while intermediate-sized 72b and small 72a particles are smaller than the average pore diameter on the inner surface of wall 70. Flow 12 arises from the feed flow 150 of the TFDF system 100. Large particles 74 pass along the inner surface of the wall 70 of the TDF 110 and into the retentate flow 180. Wall 70 includes tortuous flow paths 71 that capture certain species such as intermediate-sized particles 72b, as they pass through the wall 70. Other elements, such as small particles 72a and a portion of the flow 12 tangential to the wall 70 pass through the flow paths 71 with pore flows 160 and into permeate flows 170 through the system 100. The wall 70 of the TDF 110 includes settling zones 73 and narrowing channels 75 which trap the intermediate-size particles 72b that enter the tortuous flow paths 71 while permitting small particles 72a and pore flows 160 to pass through, resulting in separation of the intermediate-size particles 72b from the small particles 72a and the pore flows 160.

The depth-filtration process achieved in TFDF systems 100 differs from filtering processes occurring in thin-wall hollow-fiber tangential flow filtration membranes, where intermediate-size particles 72b may accumulate at the inner surface of the wall 70, resulting in the formation of a gel layer or filter cake and fouling of the filter. By contrast, TDF 110 traps intermediate-size particles 72b inside the wall 70, permitting increased volumetric throughput compared to membrane filters while permitting close to 100% passage of desired small particle species.

The thick, porous construction of wall 70 of TDF 100 relative to other filters used in the art allows high flow rates to be used, and allows TDF 100 to capture larger volume of particulate matter before fouling. That is, TDF 100 has higher "dirt loading capacity" relative to other filter elements used in the art. Dirt loading capacity is defined as the quantity of particulate matter that can be trapped by a filter before a maximum allowable back pressure is reached.

In the various embodiments of this disclosure, TDF 110 may have any suitable mean pore size (defined, for example, by bubble point testing as described in ¶43 of the '044 application, which is incorporated by reference herein). For instance, the TDF 100 may have a mean pore size ranging from 0.1 micron to 30 micron, or from 0.2 microns to 5 microns. Similarly, the TDF 100 may have any suitable wall thickness, e.g. between 0.1 mm and 5 mm, any suitable inner diameter, e.g., between 0.75 mm to 7.5 mm, typically between 1 and 3 mm, and any suitable length, e.g., between 20-200 cm.

TFDF systems are characterized by several filter parameters and operating variables. Filter parameters include TDF inner diameter (d), TDF length (l), TDF cross-sectional area (A) and number of TDF units in the filter (N). Operating variables include feed flow rate ($Q_F$), kinematic viscosity (μ), feed velocity per TDF ($V_F$), shear rate (γ) and Reynolds number (Re). Relations between filter parameters and operating variables are set forth in Table 1:

TABLE 1

Filter parameters and operating variable relations

| | | |
|---|---|---|
| TDF cross-sectional area (A) | $\dfrac{\pi \cdot d^2}{4}$ | [1] |
| Feed velocity per TDF ($V_F$) | $V_F = \dfrac{Q_F}{A \cdot N}$ | [2] |
| Shear rate (γ) | $\gamma = \dfrac{8 \cdot V_F}{d}$ | [3] |
| Reynolds number (Re) | $Re = \dfrac{V_F \cdot d}{\mu} = \dfrac{\gamma \cdot d^2}{8\mu}$ | [4] |

The Reynolds number is predictive of fluid flow behavior. When applied to fluid flows in tubular systems, laminar flows are expected where Reynolds numbers are below approximately 2300, turbulent are expected at Reynolds numbers above 4000, and a laminar-to-turbulent transition occurs between these values. While noting that laminar and turbulent flow behavior in TDFs may differ somewhat from the modeled behavior of non-permeable tubular systems, the inventors have found that TFDF systems according to this disclosure tolerate very high fluxes without fouling when the Reynolds number for the feed flow 150 is above the laminar flow range, e.g., above approximately 2300, 2500, 3000, 3500, 4000, etc. While not wishing to be bound by any theory, it is believed that turbulent feed flows may generate enhanced particle transport from the wall of TDF 110 to the bulk flow through the TDF 100, which may reduce fouling compared to laminar flows. Accordingly, various embodiments of this disclosure are directed to methods of operating TFDF systems which utilize feed flows that are turbulent or within the laminar-to-turbulent transition region, e.g., characterized by Re values above 2000, 2300, 2500, 3000, 3500, 4000, etc. Because Re increases with increases in feed velocity, shear rate and/or TDF inner diameter, certain methods of this disclosure involve operating a TFDF system with feed velocities or shear rates selected to yield Re values above 2000, 2300, 2500, 3000, 3500, 4000, etc. Because dilute aqueous solutions have a kinematic viscosity of approximately 1 centistoke (cSt), certain embodiments of the method involve operating a TFDF system under conditions in which a product of the feed velocity and the TDF diameter is greater than 2000, 2300, 2500, 3000, 3500, or 4000 mm²s⁻¹. In other embodiments, the method involves operating a TFDF system under conditions in which the feed velocity is 2000, 2300, 2500, 3000, 3500 or 4000 times greater than the quotient of the kinematic viscosity over the TDF inner diameter $$\left(\dfrac{\mu}{d}\right),$$

which is approximately equal to $$\dfrac{1}{d}$$

for dilute aqueous solutions.

Additional embodiments of the disclosure are directed to TFDF systems configured for operation under conditions in which Re values exceed 2000, 2300, 2500, 3000, 3500, 4000, etc. In certain embodiments, a product of the feed velocity and the TDF diameter is greater than 2000, 2300, 2500, 3000, 3500, or 4000 mm²s⁻¹. Other embodiments of the disclosure relate to systems configured to operate under conditions in which the feed velocity is 2000, 2300, 2500, 3000, 3500 or 4000 times greater than the quotient of the kinematic viscosity over the TDF inner diameter.

Certain embodiments of this disclosure utilize TDF geometries that are selected to promote non-laminar flow. Increases in internal diameter, for example, will tend to promote more turbulent flows at the given shear rate. The TDFs used in the embodiments of the disclosure may have inner diameters greater than 1 mm and/or walls with a thickness greater than 0.1 mm to withstand operation under high-flux conditions. Systems and methods of this disclosure may be employed in alternating tangential flow (ATF) setups, or under a constant tangential flow, and any suitable pump technology may be employed to drive feed flows. The TDF walls may have a constant or variable density and, consequently, a constant or variable average and maximum pore diameter across their length and/or circumference. The porosity of the TDFs may be further controlled by applying a coating or coatings to TDF wall surfaces. Skilled artisans will appreciate that additional modifications of TDF surfaces may be possible, including without limitation the use of affinity reagents to selectively purify specific molecular species (e.g., protein A coatings may be used to pull down human IgG).

Those of skill in the art will appreciate that, for feed flows characterized by Reynolds number at or just above the transition value of about 2300, decreases in velocity over the length of the TDFs may result in flows below the 2300 Re transition value within the TDFs. The inventors have found that improvements in filter capacity and fouling behavior are observed at Re values at the feed as low as 2300, indicating that a turbulent flow does not necessarily need to be maintained throughout the length of the TDF, and that a turbulent flow across a portion of the length of the TDF may be sufficient to improve filter capacity and fouling behavior to some degree. Thus, in certain embodiments of the disclosure, a TFDF system is operated under conditions in which $V_F$ at the feed is between 2300 and 2500, or between 2300 and 3000. In some embodiments, a TFDF system is operated such that a turbulent flow is produced across a portion of the length of the TDF units in the filter.

TFDF Systems according to the present disclosure may be used to filter a variety of fluids and separate a variety of soluble or particulate species. These include, without limitation, mammalian cells or other eukaryotic cells, microbial cells, including bacterial cells such as *E. coli*, and/or synthetic nanoparticles, such as particles for drug delivery, as well as biomolecules such as polypeptides, polynucleotides, polysaccharides, and complexes of one or more of these. Without limiting the foregoing, the systems and methods of this disclosure can be used in the production and purification of recombinant proteins such as immunoglobins or functional fragments thereof. Those of skill in the art will appreciate that the systems and methods of this disclosure may be applied in any setting in which hollow-fiber TFF systems are currently used, such as clarifying animal or microbial cultures, concentration and fractionation of species such as those described above.

Tubular Depth Filters and TFDF Systems

The embodiments of this disclosure relate, generally, to TFDF, and in some cases to TFDF systems and methods for use in bioprocessing, particularly in perfusion culture and harvest. One exemplary bioprocessing arrangement compatible with the embodiments of this disclosure includes a process vessel, such as a vessel for culturing cells (e.g., a bioreactor) that produce a desired biological product. This process vessel is fluidly coupled to a TFDF filter housing into which a TDF is positioned, dividing the housing into at least a first feed/retentate channel and a second permeate or filtrate channel. Fluid flows from the process vessel into the TFDF filter housing are typically driven by a pump, e.g., a mag-lev, peristaltic or diaphragm/piston pump, which may impel fluid in a single direction or may cyclically alternate the direction of flow.

Currently, bioprocessing systems designed to harvest a biological product at the conclusion of a cell culture period generally utilize a large-scale separation device such as a depth filter or a centrifuge in order to remove cultured cells from a fluid (e.g., a culture medium) containing the desired biological product. These large scale devices are chosen in order to capture large quantities of particulate material, including aggregated cells, cellular debris, etc. However, the trend in recent years has been to utilize disposable or single-use equipment in bioprocessing suites to reduce the risks of contamination or damage that that accompanies sterilization of equipment between operations, and the costs of replacing large scale separation devices after each use would be prohibitive.

Additionally, industry trends indicate that bioprocessing operations are being extended or even made continuous. Such operations may extend into days, weeks, or months of operation. Many typical components, such as filters, are unable to adequately perform for such lengths of time without fouling or otherwise needing maintenance or replacement.

Additionally, in bioprocessing it is often desirable to increase process yields by increasing cell density. However, increasing cell density in may be complicated by increased filter fouling, etc.

Embodiments of this disclosure address these challenges by providing economical filtration means that are tolerant of increased cell densities, extended process times, and suitable for use in harvest. The inventors have discovered that tangential flow depth filters made by melt blowing of polymers or polymer blends can be manufactured at a comparatively low-cost compatible with single use, yet are able to operate for extended periods, at high fluxes, and at increased cell densities.

Tangential flow filters in accordance with the present disclosure include tangential flow filters having pore sizes and depths that are suitable for excluding large particles (e.g., cells, micro-carriers, or other large particles), trapping intermediate-sized particles (e.g., cell debris, or other intermediate-sized particles), and allowing small particles (e.g., soluble and insoluble cell metabolites and other products produced by cells including expressed proteins, viruses, virus like particles (VLPs), exosomes, lipids, DNA, or other small particles). As used herein a "microcarrier" is a particulate support allowing for the growth of adherent cells in bioreactors.

In this regard, one of the most problematic areas for various filtration processes, including filtration of cell culture fluids such as those filtered in perfusion and harvest of cell culture fluids, is decreased mass transfer of target molecules or particles due to filter fouling. The present disclosure overcomes many of these hurdles by combining the advantages of tangential flow filtration with the advantages of depth filtration. As in standard thin wall hollow fiber filters using tangential flow filtration, cells are pumped through the lumens of the hollow fibers, sweeping them along the surface of the inner surface of the hollow fibers, allowing them to be recycled for further production. However, instead of the protein and cell debris forming a fouling gel layer at the inner surface of the hollow fibers, the wall adds what is referred to herein as a "depth filtration" feature that traps the cell debris inside the wall structure, enabling increased volumetric throughput while maintaining close to 100% passage of typical target proteins in various embodiments of the disclosure. Such filters may be referred to herein as tangential flow depth filters.

Tangential flow depth filters in accordance with various embodiments of the present disclosure do not necessarily have a precisely defined pore structure, insofar as they are aggregates of sintered particles or melt-blown polymer fibers. Particles that are larger than the "pore size" of the filter will be stopped at the surface of the filter. A significant quantity of intermediate-sized particles, on the other hand, enter the wall for the filter, and are entrapped within the wall before emerging from the opposing surface of the wall. Smaller particles and soluble materials can pass though the filter material in the permeate flow. Being of thicker construction and higher porosity than many other filters in the art, the filters can exhibit enhanced flow rates and what is known in the filtration art as "dirt loading capacity," which is the quantity of particulate matter a filter can trap and hold before a maximum allowable back pressure is reached.

Despite a lack of a precisely defined pore structure, the pore size of a given filter can be objectively determined via a widely used method of pore size detection known as the "bubble point test." The bubble point test is based on the fact that, for a given fluid and pore size, with constant wetting, the pressure required to force an air bubble through a pore is inversely proportional to the pore diameter. In practice, this means that the largest pore size of a filter can be established by wetting the filter material with a fluid and measuring the pressure at which a continuous stream of bubbles is first seen downstream of the wetted filter under gas pressure. The point at which a first stream of bubbles emerges from the filter material is a reflection of the largest pore(s) in the filter material, with the relationship between pressure and pore size being based on Poiseuille's law which can be simplified to $P=K/d$, where P is the gas pressure at the time of emergence of the stream of bubbles, K is an empirical constant dependent on the filter material, and d is pore diameter. In this regard, pore sizes determined experimentally herein are measured using a POROLUX™ 1000 Porometer (Porometer NV, Belgium), based on a pressure scan method (where increasing pressure and the resulting gas flow are measured continuously during a test), which provides data that can be used to obtain information on the first bubble point size (FBP), mean flow pore size (MFP) (also referred to herein as "mean pore size"), and smallest pore size (SP). These parameters are well known in the capillary flow porometry art.

In various embodiments, hollow fibers for use in the present disclosure may have, for example, a mean pore size ranging from 0.1 microns (μm) or less to 30 microns or more, typically ranging from 0.2 to 5 microns, among other possible values.

In various embodiments, the hollow fibers for use in the present disclosure may have, for example, a wall thickness ranging from 1 mm to 10 mm, typically ranging from 2 mm to 7 mm, more typically about 5.0 mm, among other values.

In various embodiments, hollow fibers for use in the present disclosure may have, for example, an inside diameter (i.e., a lumen diameter) ranging from 0.75 mm to 13 mm, ranging from 1 mm to 5 mm, 0.75 mm to 5 mm, 4.6 mm, among other values. In general, a decrease in inside diameter will result in an increase in shear rate. Without wishing to be bound by theory, it is believed that an increase in shear rate will enhance flushing of cells and cell debris from the walls of the hollow fibers.

Hollow fibers for use in the present disclosure may have a wide range of lengths. In some embodiments, the hollow fibers may have a length ranging, for example, from 200 mm to 2000 mm in length, among other values.

The hollow fibers for use in the present disclosure may be formed from a variety of materials using a variety of processes. For example, hollow fibers may be formed by assembling numerous particles, filaments, or a combination of particles and filaments into a tubular shape. The pore size and distribution of hollow fibers formed from particles and/or filaments will depend on the size and distribution of the particles and/or filaments that are assembled to form the hollow fibers. The pore size and distribution of hollow fibers formed from filaments will also depend on the density of the filaments that are assembled to form the hollow fibers. For example, mean pore sizes ranging from 0.5 microns to 50 microns may be created by varying filament density.

Suitable particles and/or filaments for use in the present disclosure include both inorganic and organic particles and/or filaments. In some embodiments, the particles and/or filaments may be mono-component particles and/or mono-component filaments. In some embodiments, the particles and/or filaments may be multi-component (e.g., bi-component, tri-component, etc.) particles and/or filaments. For example, bi-component particles and/or filaments having a core formed of a first component and a coating or sheath formed of a second component, may be employed, among many other possibilities.

In various embodiments, the particles and/or filaments may be made from polymers. For example, the particles and/or filaments may be polymeric mono-component particles and/or filaments formed from a single polymer, or they may be polymeric multi-component (i.e., bi-component, tri-component, etc.) particles and/or filaments formed from two, three, or more polymers. A variety of polymers may be used to form mono-component and multi-component particles and/or filaments including polyolefins such as polyethylene and polypropylene, polyesters such as polyethylene terephthalate and polybutylene terephthalate, polyamides such as nylon 6 or nylon 66, fluoropolymers such as polyvinylidene fluoride (PVDF) and polytetrafluoroethylene (PTFE), among others. Suitable polyethylene polymers include, without limitation, high-density polyethylene (HDPE) and high- or ultra-high-molecular weight polyethylene (UHMWPE)

In various embodiments, a porous wall of a filter may have a density that is a percentage of volume that the filaments take up compared to an equivalent solid volume of the polymer. For example, a percent density may be calculated by dividing the mass of the porous wall of the filter by the volume that the porous wall takes up and comparing the result, in ratio form, to the mass of a non-porous wall of the filament material divided by the same volume. A filter having a specific density percentage may be produced during manufacturing that has a direct relation to the amount of variable cell density (VCD) at which the filter can operate without fouling. A density of a porous wall of a filter may additionally or alternatively be expressed by a mass per volume (e.g., grams/cm$^3$).

Particles may be formed into tubular shapes by using, for example, tubular molds. Once formed in a tubular shape, particles may be bonded together using any suitable process. For instance, particles may be bonded together by heating the particles to a point where the particles partially melt and become bonded together at various contact points (a process known as sintering), optionally, while also compressing the particles. As another example, the particles may be bonded together by using a suitable adhesive to bond the particles to one another at various contact points, optionally, while also compressing the particles. For example, a hollow fiber having a wall analogous to the wall 70 that is shown schematically in FIG. 2 may be formed by assembling numerous irregular particles into a tubular shape and bonding the particles together by heating the particles while compressing the particles.

Filament-based fabrication techniques that can be used to form tubular shapes include, for example, simultaneous extrusion (e.g., melt-extrusion, solvent-based extrusion, etc.) from multiple extrusion dies, or electrospinning or electrospraying onto a rod-shaped substrate (which is subsequently removed), among others.

Filaments may be bonded together using any suitable process. For instance, filaments may be bonded together by heating the filaments to a point where the filaments partially melt and become bonded together at various contact points, optionally, while also compressing the filaments. As another example, filaments may be bonded together by using a suitable adhesive to bond the filaments to one another at various contact points, optionally while also compressing the filaments.

In particular embodiments, numerous fine extruded filaments may be bonded together to at various points to form a hollow fiber, for example, by forming a tubular shape from the extruded filaments and heating the filaments to bond the filaments together, among other possibilities.

In some instances, the extruded filaments may be melt-blown filaments. As used herein, the term "melt-blown" refers to the use of a gas stream at an exit of a filament extrusion die to attenuate or thin out the filaments while they are in their molten state. Melt-blown filaments are described, for example, in U.S. Pat. No. 5,607,766 to Berger. In various embodiments, mono- or bi-component filaments are attenuated as they exit an extrusion die using known melt-blowing techniques to produce a collection of filaments. The collection of filaments may then be bonded together in the form of a hollow fiber.

In certain beneficial embodiments, hollow fibers may be formed by combining bicomponent filaments having a sheath of first material which is bondable at a lower temperature than the melting point of the core material. For example, hollow fibers may be formed by combining bicomponent extrusion technology with melt-blown attenuation to produce a web of entangled biocomponent filaments, and then shaping and heating the web (e.g., in an oven or using a heated fluid such as steam or heated air) to bond the filaments at their points of contact. An example of a sheath-core melt-blown die is schematically illustrated in U.S. Pat. No. 5,607,766 in which a molten sheath-forming polymer and a molten core-forming polymer are fed into the die and extruded from the same. The molten bicomponent sheath-core filaments are extruded into a high velocity air stream, which attenuates the filaments, enabling the production of fine bicomponent filaments. U.S. Pat. No. 3,095,343 to Berger shows an apparatus for gathering and heat-treating a multi-filament web to form a continuous tubular body (e.g., a hollow fiber) of filaments randomly oriented primarily in a longitudinal direction, in which the body of filaments are, as a whole, longitudinally aligned and are, in the aggregate, in a parallel orientation, but which have short portions running more or less at random in non-parallel diverging and converging directions. In this way, a web of sheath-core bicomponent filaments may be pulled into a confined area (e.g., using a tapered nozzle having a central passageway forming member) where it is gathered into tubular rod shape and heated (or otherwise cured) to bond the filaments.

In certain embodiments, as-formed hollow fiber may be further coated with a suitable coating material (e.g., PVDF) either on the inside or outside of the fiber, which coating process may also act to reduce the pore size of the hollow fiber, if desired.

Hollow fibers such as those described above may be used to construct tangential flow filters for bioprocessing and pharmaceutical applications. Examples of bioprocessing applications in which such tangential flow filters may be employed include those where cell culture fluid is processed to separating cells from smaller particles such as proteins, viruses, virus like particles (VLPs), exosomes, lipids, DNA and other metabolites.

Such applications include perfusion applications in which smaller particles are continuously removed from cell culture medium as a permeate fluid while cells are retained in a retentate fluid returned to a bioreactor (and in which equivalent volumes of media are typically simultaneously added to the bioreactor to maintain overall reactor volume). Such applications further include clarification or harvest applications in which smaller particles (typically biological products) are more rapidly removed from cell culture medium as a permeate fluid.

Hollow fibers such as those described above may be used to construct tangential flow depth filters for particle fractionation, concentration and washing. Examples of applications in which such tangential flow filters may be employed include the removal of small particles from larger particles using such tangential flow depth filters, the concentration of microparticles using such tangential flow depth filters and washing microparticles using such tangential flow filters.

EXAMPLES

Certain principles of the disclosure will be further illustrated by the following non-limiting examples:

Example 1: Reduced Fouling and Increased Flux in TFDF Systems with Increased TDF Internal Diameters A filtration process was designed to generate non-laminar cross-flows in the TFDF setup. This was achieved by selecting a combination of TDF geometry parameters and process conditions to yield a Reynolds number greater than 2300 as calculated at the inlet of the filter. Manipulation of TDF diameter and inlet flow rate were found to be sufficient to achieve the desired Reynolds numbers, and turbulent flow effects were observed in TDFs with inner diameters greater than 1 mm with flow rates selected to yield Re values above 2300 (e.g., $V_F$>2 m/s). In TDFs with inner diameters greater than 1 mm, it was found that shear rates commonly used in TFF processes (<16,000 $s^{-1}$) were effective in creating turbulent flows.

In addition to having an inner diameter greater than 1 mm, it was observed that wall thicknesses above 0.1 mm may be useful in maintaining the structural integrity of the filter under high flux conditions.

Figure 4:
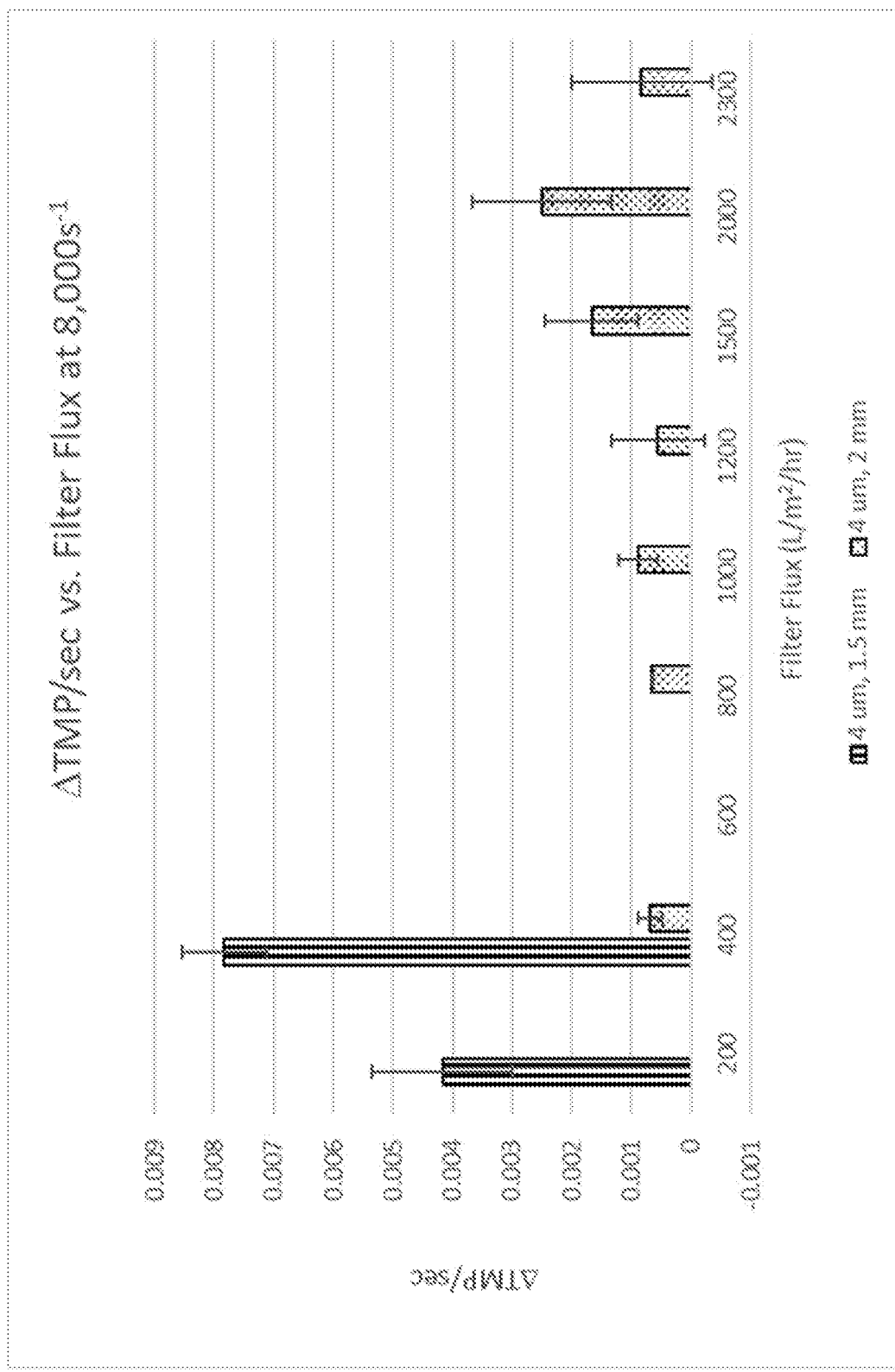
FIG. 4 is an empirical comparison of transmembrane pressure change (ΔTMP/sec—an indicator of gel layer formation or filter fouling) and filter flux for two TFDF systems of the present disclosure. Shear rate (γ) is held constant at $8000s^{-1}$ in both conditions. In the 1.5 mm filter diameter system, fouling occurs at fluxes above 400 $Lm^{-2}$ $hr^{-1}$, while in the 2.0 mm system, fluxes up to 2300 $Lm^{-2}$ $hr^{-1}$ are tolerated without fouling.

FIG. 4 shows changes in transmembrane pressure (ATMP/sec) observed at varying filter fluxes in TFDF systems utilizing 1.5 mm or 2.0 mm TDF internal diameters. Significant increases in ATMP/sec are indicative of the formation of a gel layer on the inner surfaces of the tubular filtration elements (in this case TDFs) and signal fouling of the filter. The figure shows that, when operated at a fixed shear rate of 8000 s-1, the 1.5 mm TFDF setup exhibited fouling at fluxes above 400 L■$m^{-2}$■$hr^{-1}$, while the 2 mm TFDF setup exhibited no appreciable fouling at fluxes up to 2300 L■$m^{-2}$■$hr^{-1}$. Table 2, below, lists filter parameters and operating variables for both conditions; the systems differed principally in their respective TDF diameters and their Reynolds numbers at the feed, though different feed flow rates were used to achieve the same shear rate in both systems.

TABLE 2 filter parameters and operating variables for 1.5 and 2 mm TFDF systems

|  | 1.5 mm system | 2 mm system |
| --- | --- | --- |
| TDF diameter (d) | 1.5 mm | 2.0 mm |
| Kinematic viscosity (μ) | 1.0 cSt | 1.0 cSt |
| TDF cross-sectional area (A) | 1.767 $mm^2$ | 3.142 $mm^2$ |
| Feed flow rate ($Q_F$) | $160\frac{mL}{min}$ | $377\frac{mL}{min}$ |
| Feed Velocity ($V_F$) | $1.509\frac{m}{s}$ | $2\frac{m}{s}$ |
| Shear Rate (γ) | 8048.131 $s^{-1}$ | 8000.188 $s^{-1}$ |
| Reynolds Number at feed ($Re_F$) | 2263.537 | 4000.094 |

Figure 3:
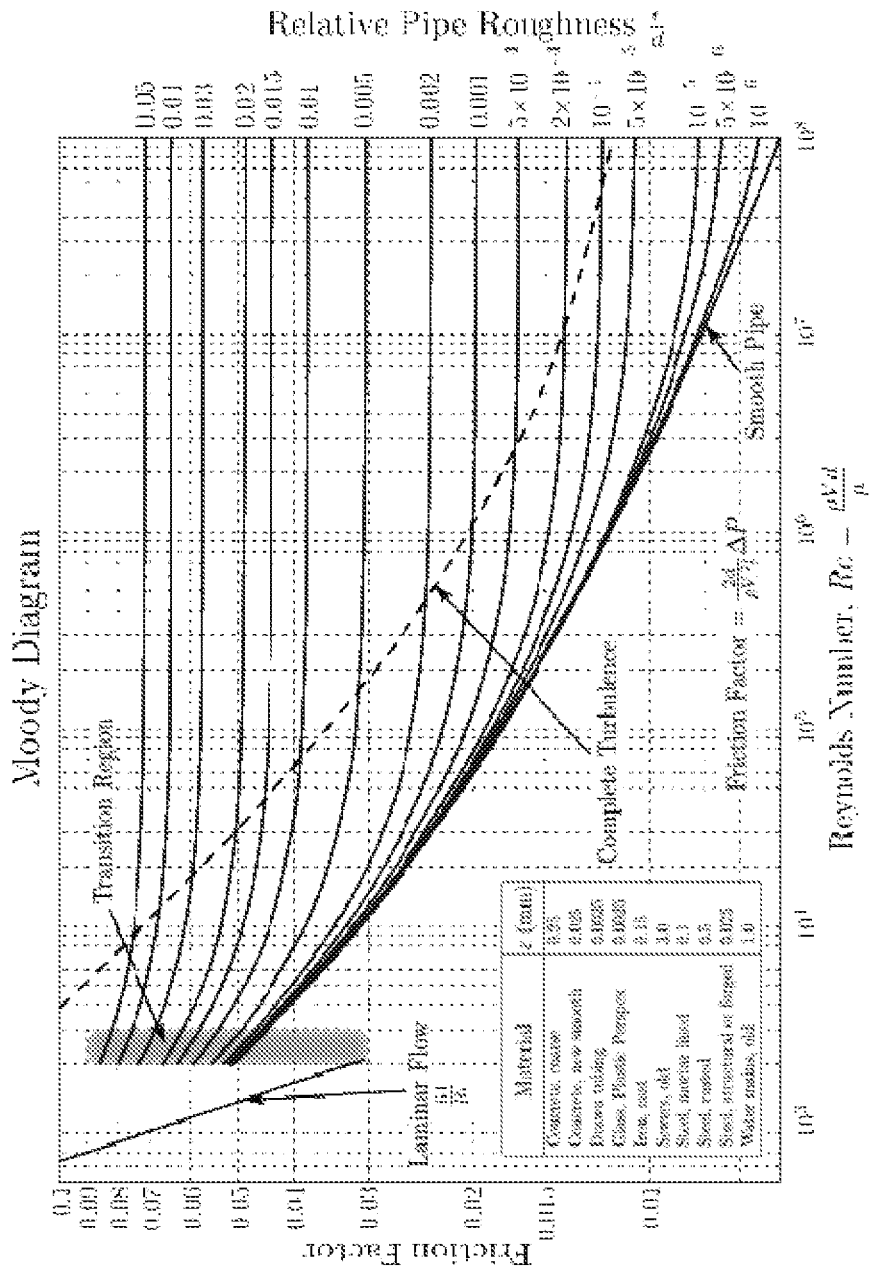
FIG. 3 is a Moody diagram plotting friction factor [$f_D$] vs. Reynolds number [$R_e$] over varying circular pipe roughnesses by Beck and Collins.

As Table 2 and the Moody Diagram of FIG. 3 illustrate, when feed flows are adjusted to maintain a constant shear rate of about 8000 $s^{-1}$, the 2 mm system would be expected to exhibit turbulent flow at the feed based on the $Re_F$ of 4000, while the feed flow in the 1.5 mm system would be expected to be laminar at an $Re_F$ of approximately 2000.

CONCLUSION

The foregoing disclosure has presented several exemplary embodiments of TFDF systems according to the present disclosure. These embodiments are not intended to be limiting, and it will be readily appreciated by those of skill in the art that various additions or modifications may be made to the systems and methods described above without departing from the spirit and scope of the disclosure. Additionally, while the foregoing disclosure has focused primarily on tangential flow depth filtration systems and their applications, it will be appreciated by those of skill in the art that the principles of the disclosure are applicable to other systems including conventional hollow-fiber TFF systems.

What is claimed is:

1. A method of filtering a fluid, comprising:
   passing the fluid through a filter having first and second ends and comprising at least one tubular depth filter unit (TDF) extending between and open to each of the first and second ends of the filter, the at least one TDF comprising an inner diameter of at least 1 mm and comprising a porous wall having a thickness of at least 100 μm;
   wherein passing the fluid comprises the fluid flowing in a non-laminar manner through the at least one TDF.
2. The method of claim 1, further comprising collecting a permeate of the filter, the permeate comprising a non-desired species at least 10× less than a concentration of the non-desired species in the fluid.

3. The method of claim 1, wherein a product of a feed velocity of the fluid and an inner diameter of at least one fiber is greater than 2500 mm2s−1.

4. The method of any of claim 1, wherein a Reynolds number characterizing the flow of fluid into the filter is greater than 2000.

5. The method of claim 1, wherein a feed velocity of the fluid is 2000 times greater than a quotient of a kinematic viscosity of the fluid over the inner diameter of the TDF.

6. The method of any of claim 5, further comprising collecting a permeate of the TDF, the permeate comprising a concentration of a desired species that is at least 10× greater than a concentration of the desired species in the fluid.

7. The method of claim 5, further comprising collecting a permeate of the TDF, the permeate comprising a concentration of a non-desired species that is at least 10× less than a concentration of the non-desired species in the fluid.

8. The method of any of claim 5, wherein the TDF retains a non-desired species.

9. The method of claim 8, wherein the retained non-desired species is selected from the group consisting of a species of mammalian cell origin, a species of microbial cell origin, a species of viral origin, a protein, a nucleic acid, a polysaccharide, and a complex of any of the foregoing.

10. The method of claim 5, wherein a desired species passes through the TDF into a permeate.

11. The method of claim 10, wherein the desired species is selected from the group consisting of a species of mammalian cell origin, a species of microbial cell origin, a species of viral origin, a protein, a nucleic acid, a polysaccharide, a virus, a microcarrier, a particle, and a complex of any of the foregoing.

12. A composition comprising a permeate or a filtrate collected according to the method of claim 11.

13. The method of claim 5, further comprising removing a permeate from the fluid, thereby increasing a concentration of a desired species that is retained by the TDF, wherein the concentration of the desired species is increased by 5×.

14. A composition comprising a permeate or a filtrate collected according to the method of claim 13.

15. The method of claim 1, wherein passing the fluid comprises passing a cell culture media tangentially through the TDF, wherein passing the cell culture media comprises introducing a non-laminar fluid flow through the first end of the TDF by operating a system comprising the TDF at a filter flux above 400 $Lm^{-2}h^{-1}$ (LMH) and a shear rate of less than 16,000 $s^{-1}$.

16. The method of claim 2, wherein a Reynolds number of the flow through the first end is greater than about 2300.

17. The method of claim 2, wherein the TDF comprises a porous polymer wall comprising a density of about 50%, 51%, 52%, 53%, 54%, 55%, 56%, 57%, 58%, 59%, or 60% of a density of an equivalent solid volume of the polymer.

18. The method of claim 2, wherein a product of a feed velocity of the flow through the first end and an inner diameter of the at least one TDF is greater than 2500 mm2s−1.

19. The method of claim 2, wherein the non-desired species is selected from the group consisting of: a species of mammalian cell origin; a species of microbial cell origin; a species of viral origin; a protein; a nucleic acid; a polysaccharide; or a complex of any of the foregoing.

* * * * *